United States Patent [19]

Fan et al.

[11] Patent Number: 5,295,978

[45] Date of Patent: Mar. 22, 1994

[54] BIOCOMPATIBLE HYDROPHILIC COMPLEXES AND PROCESS FOR PREPARATION AND USE

[75] Inventors: You-Ling Fan, East Brunswick; Lawrence Marlin, Bridgewater, both of N.J.

[73] Assignee: Union Carbide Chemicals & Plastics Technology Corporation, Danbury, Conn.

[21] Appl. No.: 635,914

[22] Filed: Dec. 28, 1990

[51] Int. Cl.$^5$ .............................................. A61M 25/00
[52] U.S. Cl. ......................................... 604/265; 427/2; 606/129; 623/11
[58] Field of Search ................... 427/2, 393.5, 412.1, 427/379, 407.1; 623/1, 11; 428/423.1; 604/265, 266; 606/129

[56] References Cited

U.S. PATENT DOCUMENTS

| | | | |
|---|---|---|---|
| 4,100,309 | 7/1978 | Micklus | 427/2 |
| 4,119,094 | 10/1978 | Micklus et al. | 128/132 |
| 4,373,009 | 2/1983 | Winn | 428/424 |
| 4,589,873 | 5/1986 | Schwartz et al. | 604/265 |
| 4,642,267 | 2/1987 | Creasy et al. | 428/413 |
| 4,666,437 | 5/1987 | Lambert | 604/265 |
| 4,707,381 | 11/1987 | Toyama et al. | 427/393.5 |
| 4,729,914 | 3/1988 | Kliment et al. | 428/36 |
| 4,835,003 | 5/1990 | Becker et al. | 427/2 |
| 4,965,112 | 10/1990 | Brinkman et al. | 427/2 |
| 4,980,231 | 12/1990 | Baker et al. | 427/393.5 |
| 4,990,357 | 2/1991 | Karakelle et al. | 427/2 |
| 5,037,677 | 8/1991 | Halpern et al. | 427/2 |
| 5,084,315 | 1/1992 | Karimi et al. | 427/2 |
| 5,091,205 | 2/1992 | Fan | 427/2 |
| 5,135,516 | 8/1992 | Sahatjian et al. | 427/412.1 |

Primary Examiner—Shrive Beck
Assistant Examiner—Diana L. Dudash
Attorney, Agent, or Firm—W. K. Volles

[57] ABSTRACT

Biocompatible polymeric complexes having utility in many fields including medical applications, as well as personal and health care, are provided and can be affixed to a variety of substrate materials which themselves may or may not also be biocompatible. The complexes of this invention are comprised of a carboxylic acid polymer with either a poly(lower-alkylene oxide) or a poly(N-vinyl lactam). Moreover, a complex of an antimicrobial agent such as iodine can be formed with the complex to provide antimicrobial activity. The complexes are also useful for forming biocompatible coatings on medical devices, some of which can render the surface lubricious when exposed to aqueous or body fluids.

45 Claims, No Drawings

BIOCOMPATIBLE HYDROPHILIC COMPLEXES AND PROCESS FOR PREPARATION AND USE

BACKGROUND OF THE INVENTION

1) Field of the Invention

This invention relates in general to biocompatible hydrophilic polymeric complexes. In one aspect this invention relates to biocompatible hydrophilic polymeric complexes which can be affixed to numerous substrates and therefore render them particularly useful for a variety of applications, particularly in the medical device, personal care, and health care fields. In a further aspect, the invention is directed to coated substrate materials wherein the substrate material may not itself be biocompatible, but since it possesses desirable physical and other properties, when coated with the polymeric complex it is then ideally suited for use in areas where biocompatibility is desired. In a still further aspect, this invention is directed to combinations of the complexes with biologically active agents, such as antimicrobial agents as well as to processes for their preparation.

2) Description of the Related Art

For many applications it is desirable to have a hydrophilic polymeric surface which is biocompatible with the animal and human body. However, many polymeric surfaces due to their chemical composition or method of preparation are not compatible with the body and hence they are not suitable for use in fields such as medical devices, personal care, health care, pharmaceuticals, and other areas of interest.

In addition, it is desirable that the hydrophilic polymer be firmly attached to the substrate such that it exhibits good abrasion resistance. Historically, techniques used to attach a polymer to a substrate include chemical treatment such as chemical cross-linking or exposure to a high energy radiation source, such as an electron beam machine. These methods are not usually desirable. A highly cross-linked composition prepared by any one of these techniques can often result in a different chemical composition from that of the parent polymer and therefore, such polymers might have a potentially different biological behavior. Furthermore, high-energy cross-linking often leads to polymer degradation and discoloration. Thus, the conventional cross-linking techniques are not particularly suited for preparing a polymeric coating from a biocompatible material since there is no assurance that the final coating will still possess the desired biocompatibility, physical properties, or both.

Of the many known natural and synthetic polymeric hydrophilic systems, two polymeric compounds are particularly noted for their biocompatibility and have found wide acceptance in a variety of areas where such biocompatibility is desired. One such known polymeric compound, poly(vinyl pyrrolidone), has an exceptionally low animal oral toxicity and a high parental lethal dose ($LD_{50}$) and accordingly, has found extensive application in the pharmaceutical industry. For example, the United States Pharmacopeia, 22nd Revision, Jan. 1, 1990, discloses on page 1118 the product Povidone, which is a linear synthetic polymer consisting of poly(vinyl pyrrolidone). It is indicated that this polymer when complexed with iodine is useful as an ointment and as a topical anti-infective aerosol solution.

The biocompatibility of poly(vinyl pyrrolidone) is also mentioned in an article "Acetylene Derived Polymers", by S. C. Johnson, Cosmetics and Toiletries, Vol. 99, Jun. 14, 1984, pp 77-81.

A second well known class of polymeric compounds which are characterized by excellent biocompatibility with animals and humans, are the poly(ethylene oxides), particularly the high molecular weight ethylene oxide polymers. The biocompatibility of poly(ethylene oxide) with blood has been studied and reported in several journals, such as, for example, an article by George, J. N., Direct Assessment of Platelet Adhesion to Glass; study of the forces of interaction and the effects of plasma and serum factors, platelet function and modification of the glass surface, Blood, 40, 862, 1972.

Other articles include, Wasiewski, W., Rasio, M. J., Martin, B. M., Detwiler, J. C., and Fenton, J. W., Thrombin Absorption to Surfaces and prevention with PEG 6000, Thromb. Res., 8, 881, 1976, and S. W. Kim and J. feijen, "Critical Reviews in Biocompatibility", D. F. Williams, Editor, CRC Press, Inc., Boca Raton, Fla., Vol 1, issue 3, pp 229-260.

However, even though both poly(vinyl pyrrolidone) and poly(ethylene oxide) have excellent biocompatible properties with the human body, they do not readily adhere to substrates which might find application in the medical, personal care, health care, or pharmaceutical fields. Accordingly, prior to the present invention, substrates which are not normally biocompatible were rarely utilized in areas involving the human body even though they may possess desirable features of strength and mass which would otherwise render them suitable for such purposes.

A poly(lower-alkylene oxide) or a poly(N-vinyl lactam), such as poly(vinyl pyrrolidone), can be immobilized through complexation with a carboxylic acid-containing polymer on the surface of a variety of substrates forming an abrasion resistance, biocompatible coating. In some instances, the coatings also offer a high degree of lubricity in aqueous and body fluids such as blood. Since the complexes are formed through a relatively weak hydrogen bond or dipole-dipole interactions, the chemical compositions and properties of the parent polymer are largely preserved. Hence, the disadvantages of chemical cross-linking and other methods mentioned above are largely avoided. These biocompatible surfaces can be further formulated with additives, such as antimicrobial agents, to yield novel coated substrates having antimicrobial properties.

Accordingly, one or more of the following objects will be achieved by the practice of this invention. It is an object of this invention to provide biocompatible, polymeric abrasion resistant surfaces. Another object is to provide substrates coated with the polymeric complexes so that the outer exposed surface is biocompatible with its surrounding environment. A further object of this invention is to provide substrate materials, such as medical devices having a coating of a polymeric compound which is biocompatible. A further object is to provide substrates coated with the polymeric complexes and which contain additives such as antimicrobial agents and other pharmaceutically effective agents. A still further object of this invention is to provide processes for the preparation of the coated substrates. Another object is to provide medical and other devices and instruments which have a coating of a biocompatible material which becomes lubricious upon exposure to body fluids. These and other objects will readily be-

SUMMARY OF THE INVENTION

In its broad aspect, this invention is directed to an abrasion resistant, biocompatible polymer coated substrate, such as those used in medical devices, personal care, health care, and in the pharmaceutical field. In some instances the complexes may have a lubricious coating which becomes slippery upon exposure to an aqueous fluid such as body fluids. The invention is also directed to a method for preparing the complexes and the coated substrates.

The method for preparing the coated substrates comprises the steps of:

(1) contacting a substrate with a polyisocyanate contained in at least one first inert solvent to provide at least a partially coated substrate;

(2) contacting the coated substrate with a carboxylic acid-containing polymer contained in at least one second inert solvent to provide a multiple coated substrate;

(3) contacting the multiple coated substrate with at least one third inert solvent containing a biocompatible poly(N-vinyl lactam) or a poly(lower-alkylene oxide), and (4) thereafter drying the multiple coated substrate to provide a biocompatible coating.

In the present invention a satisfactory polymeric coating on a substrate should exhibit a high degree of abrasion resistance which is related to its adhesion to the substrate. High molecular weight poly(ethylene oxide) and poly(vinylpyrrolidone) are difficult to bond to the surface of many materials because of a lack of sufficient reactive end groups. Consequently, coatings made from any of these polymers alone usually would not have adequate abrasion resistance. This shortcoming is overcome by the method of the present invention where these biocompatible complex polymers are immobilized by complexation with a precoat containing a suitable carboxyl-containing polymer. The poly(ethylene oxide) and/or poly(vinyl pyrrolidone) polymers have good biocompatibility and are also ideally suited for complexing with other additives.

By the term "abrasion resistance" as used throughout the specification and appended claims is meant the ability of the water soluble polymer to resist leaching and mechanical abrasion as evidenced by its ability to maintain a hydrophilic surface. The hydrophilicity of the surface is determined by putting a water droplet on the surface and observing its physical shape. When the droplet is retained at an apparent high contact angle, leaching and/or abrasion of the surface has occurred. On the other hand, a hydophilic surface is still present on the surface of the substrate which has been coated in accordance with this invention, when there is rapid spreading of the water droplet which indicates an apparent low contact angle.

DESCRIPTION OF THE PREFERRED EMBODIMENTS

The polymeric complexes of this invention are conveniently prepared by contacting a substrate with a polyisocyanate such as toluene diisocyanate, in a first liquid medium, optionally drying the coating, contacting the coated substrate with a carboxylic acid-containing polymeric compound in a second liquid medium, optionally drying the coating, and finally coating the multiple coated substrate with a poly(N-vinyl lactam) or a poly(lower-alkylene oxide). In some instances, it is possible to combine the first two steps or the second and third steps depending upon the particular components and solvents employed.

After drying, a non-tacky, easy-to-handle, and uniformly coated substrate is obtained. In some instances, depending upon the type and relative ratio of the two polymeric components, the surface of the substrate after coating becomes lubricious instantly upon exposure to an aqueous medium such as body fluids.

For such applications wherein a lubricious coating is desired on the substrate, the desired substrate material is contacted with a polyisocyanate such as a toluene diisocyanate in a liquid medium. The liquid medium can be removed by drying or the substrate can be treated directly with a high molecular weight poly(carboxylic acid) in a liquid medium. After drying in an oven, the final coating of the poly(N-vinyl lactam) or the poly(lower-alkylene oxide) is applied preferably from an organic solvent and uniformly coated substrate is obtained. For example, if the substrate is a catheter, the surface of the resultant catheter becomes lubricious instantly upon exposure to an aqueous solution or body fluids. The degree of lubricity varies depending on the type and relative ratio of the two polymeric components.

In addition to a quick initial lubricity, the hydrophilic lubricious coating obtained by this aspect of the invention is resistant to abrasion. Consequently, a catheter coated in accordance with the teachings of this aspect of the invention will retain a lubricious surface for a long duration which is often required during the course of a medical procedure.

The term "bath" as employed throughout the specification and appended claims is meant to include not only solutions of the indicated organic compounds, but dispersions and emulsions.

Application of the coatings from the bath can be effected by a variety of methods and includes, but is not limited to, dipping, spraying, electrical deposition, painting and the like. Optionally, the coated substrate can be further treated with an aqueous bath to partially or totally neutralize the free acid. In those instances wherein the substrate is subjected to high temperatures, such as in thermoforming processes, the treatment with the aqueous bath to effect neutralization or partial neutralization is desired.

As indicated above, the hydrophilic lubricious coating of this invention is comprised of three components; a polyisocyanate primer, and a water-soluble or water dispersible polycarboxylic acid coating, and finally a poly(N-vinyl lactam) or a poly(lower-alkylene oxide). They are normally applied in three separate coating steps. However, if desired, the drying step after application of the polyisocyanate coating can be omitted and drying effected after application of the second coat or even after the top coat. Also, as indicated previously, two of the coating steps can be effected at the same time. Thus, the first two steps, or the second and third steps, can be combined into separate steps.

In the first step of this invention, the solvents useful for applying the polyisocyanates to a substrate include methyl ethyl ketone, ethyl acetate, ethyl lactate, chloroform, trichloroethylene, dichloromethane, hexane, heptane, toluene, their mixtures with mineral oil, or other suitable organic solvents which do not react with isocyanates under the coating conditions. The preferred solvent is methyl ethyl ketone.

Alternatively, the polyisocyanates can be dispersed in a solvent/non-solvent mixture to form a dispersion or emulsified to form an oil-in-water emulsion. When an emulsion is used, the reactive isocyanate groups need to be protected by suitable chemical groups known to those skilled in the art.

A wide variety of polyisocyanates can be employed in preparing the coatings of the present invention and include, but are not limited to, toluene-2,3-diisocyanate, toluene-2,6-diisocyanate, commercial mixtures of toluene-2,4- and 2,6-diisocyanates, 4,4'-diphenylmethane diisocyanate, cyclohexylene-1,4-diisocyanate, m-phenylene diisocyanate, 3,3-diphenyl-4-biphenylene diisocyanate, 4,4-biphenyl diisocyanate, 1,6-hexamethylene diisocyanate, 1,5-naphthalene diisocyanate, cumene-2,3-diisocyanate, 2,4-diisocyanatodiphenylether, 5,6-dimethyl-1,3-phenylenediisocyanate, 2,4-dimethyl-1,3-phenylenediisocyanate, 2,4-dimethyl-1,3-phenylenediisocyanate, 4,4-diisocyanatodiphenylether, 9,10-anthracene diisocyanate, 2,4-diisocyanatotoluene, 1,4-anthracene diisocyanate, 2,4,6-toluene triisocyanate, isophorone diisocyanate, and p,p',p"-triphenylmethane triisocyanate, and the like. Equally useful are isocyanate end-capped prepolymers and adducts, isocyanate end-capped polyfunctional aromatic adducts, isocyanate end-capped polyfunctional aliphatic adduct and two component systems such as end capped aliphatic polyester polyol and aliphatic polyol compound, and their mixtures with different polyisocyanates as described above.

Illustrative of isocyanate end-capped adducts are the reaction products of 2,4-tolylene diisocyanate, 4,4'-diphenylmethane diisocyanate, polymethylenepolyphenyl isocyanate, or 1,5-naphthylene diisocyanate, with 1,2-polypropylene glycol, polytetramethylene ether glycol, 1,4-butanediol, 1,4-butylene glycol, 1,3-butylene glycol, poly(1,4-oxybutylene) glycol, caprolactone, adipic acid esters, phthalic anhydride, ethylene glycol, diethylene glycol, and the like.

The polymers suitable for use in forming the second coatings of the present invention are carboxylic acid-containing polymers. The polymer can be a free acid or partially neutralized as represented by the following formula:

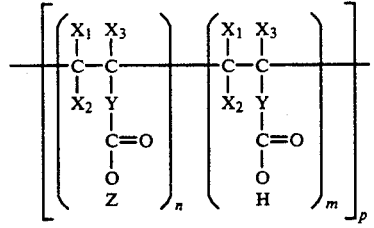

where $n = 0-0.95$ mole fraction of neutralized acid moieties;

$m = 0.05-1.0$ mole fraction of acid moieties with the proviso that $n + m = 1$;

$X_1$, $X_2$, $X_3$ are each a hydrogen atom or a suitable monovalent organic radical, such as lower alkyl or cycloalkyl or aryl of up to 8 carbon atoms, and wherein the X groups are such that the polymer remains water soluble;

Y is either a single bond or any suitable divalent organic radical, such as a hydrocarbon group of up to 8 carbon atoms, provided it does not adversely affect the solubility of the polymer;

Z is either a metallic ion or a suitable ammonium ion; and p is a very large number such that the polymer has a molecular weight between about 200,000 and about 5,000,000.

Even though all poly(carboxylic acid) homopolymers can be useful to different degrees, the high molecular weight polymers are more desirable. The useful molecular weights range from 200,000 to about 5,000,000. Representative carboxylic acid containing homopolymers include, but are not limited to, poly(acrylic acid), poly(methacrylic acid), poly(isocrotonic acid), and the like. The poly(carboxylic acid) of this invention can be either linear or partially cross-linked such that it would form either a solution or a colloidal dispersion in the coating medium. The preferred poly(carboxylic acid) polymer is a poly(acrylic acid) having a molecular weight of from about 200,000 to about 5,000,000. Particularly preferred poly(carboxylic acid) polymers include poly(acrylic acid) polymers having molecular weights of from about 1,000,000 to about 3,000,000.

Olefinic acids such as acrylic acid can be copolymerized with one or more of other unsaturated monomers to produce copolymers containing carboxylic acid moieties. Examplary copolymers include Carboset and Surlyn produced by B. F. Goodrich and DuPont respectively. Copolymers containing water-insoluble units as well as carboxylic acid units can be mixed with the homopolymers if so desired, as long as they are compatible.

Polyampholytes which contain one or more polymeric acids mentioned above may be also useful for the purpose of this invention as long as the basic moiety is a tertiary amine.

Any organic solvents or mixed solvents for the poly(carboxylic acid) polymers used in this invention may be employed for making the second solution provided that they are not reactive with the polyisocyanates. Examplary solvents or solvent mixtures include acetonitrile, N,N-dimethyl formamide (DMF), acetonitrile-DMF, acetyl acetone, acrylonitrile, benzonitrile, diethyl acetamide, diethyl formamide, diethylformamide-DMF, dimethyl acetamide, 1,4-dioxane, dipropyl sulfone, DMF-acetone, DMF-toluene, DMSO (dimethyl sulfoxide), DMSO-DMF, ethyl formamide, N-methyl-2-pyrrolidone, nitrobenzene, nitrobenzene-DMF, phenylacetate, propionitrile, styrene, and the like. The dissolution of poly(carboxylic acid) polymers in many of the above-mentioned solvents may be enhance by the addition of suitable amines. The preferred solvent is dimethyl formamide.

To prepare a seed-free poly(carboxylic acid) solution, it is advantageous to add a small amount of surfactant in the solvent before mixing with the polymer. Any soluble surfactant or a mixture of surfactants in the above-mentioned solvents may be useful. The preferred surfactants are soluble non-ionic surfactants such as polyoxyethylene sorbitan fatty acid esters, polyoxyethylene acids, polyoxyethylene alcohols, fluorinated alkyl esters, fluorinated alkoxylates and their mixtures.

Due to the high molecular weight of the poly(carboxylic acid) polymers preferred for use in the present invention, their solution viscosities may be too high to be suitable for some coating processes. It is advantages in these instances to convert the polymer solution to a colloidal dispersion by mixing with one or more non-solvents. Exemplary non-solvents include tertiary alcohols, ketones, aliphatic ethers, aliphatic and aromatic hydrocarbons. The preferred non-solvents are acetone, methyethylketone (MEK) and tertiary butyl alcohol.

Alternatively, the poly(carboxylic acid) may be emulsified to a water-in-oil emulsion. An example for forming such a water-in-oil emulsion is described in U.S. Pat. No. 4,618,647.

The final coating which is applied to the substrate in accordance with the teachings of the present invention, is a poly(N-vinyl lactam) or a poly(lower-alkylene oxide) compound, and which is capable of forming a hydrogen bonded complex with a water-soluble carboxylic acid-containing polymer. All that is necessary is that the final coating be biologically compatible with the human body. As indicated, one of the polymeric compounds is preferably a poly(vinyl pyrrolidone) and the other a poly(ethylene oxide). In the process of the present invention the poly(lower-alkylene oxide) compounds are preferably the polymers and copolymers of 1,2-alkylene oxides, and particularly the high molecular weight poly(ethylene oxide) and copolymers thereof. These polymers can be block or random copolymers.

Accordingly, illustrative polymers which can be employed as the final coating in the present invention include, among others, olefin polymers, e.g., ethylene oxide homopolymer, ethylene oxide copolymers comprised of at least 50 weight percent ethylene oxide in copolymerized form with up to 50 weight percent of at least one other olefin oxide, such as propylene oxide, butylene oxide, pentylene oxide, and the like.

If desired, one can use other oxygen-containing polymeric compounds in combination with poly(vinyl pyrrolidone) or poly(ethylene oxide) as long as such other compounds are biocompatible. Such compounds include polymers such as methyl cellulose, carboxymethylcellulose, sodium carboxymethylcellulose, hydroyethylcellulose, and the like; polyvinyl alcohol, maleic anhydride-vinylether copolymers, ethylenemaleic anhydride copolymers, dextran, gelatin, hydropropylcellulose, hydroxyethylcarboxymethylcellulose, propyleneglycol alginate, and the like.

Among the nitrogen-containing polymeric compounds poly(vinyl pyrrolidone) is preferred although other poly(N-vinyl lactams) which may contain lower alkoxy or lower alkyl substituents may be used.

If so desired, the polymeric coating can be cross-linked to improve durability by high energy radiation, such as, electron beam or plasma radiation.

For some applications it might be desirable to incorporate one or more additives in the coatings particularly the primer coating. For example, some substrates, such as catheters are comprised of a thermoplastic rubber and it is preferred that the primer coating contain a plasticizer to minimize loss of flexibility due to the coating operation. A wide variety of plasticizers can be employed such as the esters of fatty acids, mineral oil or silicone oil. The plasticizer must, of course, be compatible with the components of the coatings and have no undersirable biological properties which would limit their use.

Other additives can be employed in the coatings in addition to the surfactants such as, stabilizers, antioxidants, antimicrobial agents, colorants, biological components and the like. For example, in catheters which are inserted into blood vessels, it may be desirable to have contained in the coating an antithrombogenic agent such as heparin, to avoid blood clot formation during the surgical procedure. The antithrombogenic agent can be used either as an additive or as a chemically bonded moiety of the final coating.

For applications wherein articles are coated and used in the body, it may also preferred to incorporate an antimicrobial agent into the final coat. It has been observed that iodine can easily be incorporated into the final coating and forms a complex which provides active iodine available as an antimicrobial compound. Other antimicrobial agents as well as a variety of other pharmaceutically acceptable agents can also be used.

As previously indicated, the present invention can be utilized to coat a wide variety of substrate materials. Since the coating provides a biocompatible surface it is possible to entirely coat a substrate which itself is not biocompatible and therefore utilize the desirable features of the substrate material which might not otherwise be available. For example, the fabrication of prosthetic devices, catheters, guide wires and the like used in the medical field has largely been limited to materials which are known to be inert and which do not affect the body. By utilization of the present invention materials which otherwise might not be suitable can now be used and advantage taken of their unique properties.

Accordingly, materials such as acrylates, nylon, polypropylene, silicone rubbers thermoplastic rubbers (such as butadiene styrene copolymers), polyesters (such as Dacron), stainless steel, cobalt-chromium alloys, platinum, polyethylene, pryolytic carbon disks or balls, segmented polyurethanes, alumina, polysulfone, bioglass, and the like, can be employed.

The techniques employed in coating the substrates are not necessarily critical and any coating processes suitable for making thin coatings may be utilized. For operations where the shelf-life of the coating solutions is not a critical issue, a single solution system containing a blend of both polyisocyanate and poly(carboxylic acid) may sometimes be used in a single coat operation. Thereafter the final coating of poly(vinyl pyrrolidone) or poly(ethylene oxide) can be applied.

In practice it has been found that excellent adhesion and abrasion resistance properties are obtained when the total thickness of the primer and top coating applied to the substrates in accordance with the teachings of this invention is from the submicron range to a few microns.

The concentration of the isocyanate and the carboxylic acid-containing polymer in the first and second respective coating solutions can vary depending upon the particular components employed, their solubility as well as other considerations. In general the polyisocyanate component in the primer coating is contained in the coating solvent in an amount of at least about 0.01% by weight. If the polyisocyanate is in liquid form, it can be employed without a solvent. However, in practice, it is preferred to employ the polyisocyanate in a solvent in a concentration of from about 0.1 to about 20% by weight, and more preferably from about 1 to about 5% by weight.

The amount of the poly(carboxylic acid) component employed in the solvent will be controlled by the viscosity of the medium. Most any concentration can be used as long as it is high enough to permit the preparation of a satisfactory coating, and yet is low enough so that the solution is not too viscous. Concentrations of from about 0.1 to about 10% by weight are preferred with a concentration within the range of about 0.5 to about 5% by weight the most preferred. In practice, the stoichiometry is such that the molar ratio of carboxylic acid groups to isocyanate groups is in excess and will be greater than about 1:1.

In practice, the final coating is usually applied in a thickness of from about 0.05 to about 10 microns and more preferably from about 0.1 to about 5 microns. The third solvent system for application of the final coating is one which is compatible with the other solvent systems and includes, among others, both organic and aqueous systems. In practice, when a lubricous coating is desired, it is preferred that either an aqueous or an organic solvent be utilized. Illustrative compounds which can be utilized as a solvent for the final coating include water and organic solvents such as, methylene chloride, 1,1-dichloroethane, 1,2-dichloroethane, 1,1,1-trichloroethane, 1,1,2-trichloroethane, 1,1,2,2-tetrachloroethane, toluene, benzene, chloroform, alcohols, esters, DMF, cyclohexane, water, pyridine, acetone, acids, nitromethane and the like.

In general the polymeric compound comprising the final coating is contained in the solvent in a concentration of from about 0.01 to about 10 weight per cent and more preferably from about 0.1 to about 2 weight percent.

Although the drying temperatures and times are not necessarily critical, it has been found that the coated substrate can be dried at temperatures of from about 20° to about 150° C. and more preferably from about 50° to about 100° C. Drying periods can range from a few seconds to 24 hours or more.

As previously indicated, a variety of substrate material can be coated in whole or in part with a biocompatible coatings of the polymeric complex. By choice of proper polymeric compounds, the coating can be obtained which is dry to the touch yet becomes quite lubricious when exposed to fluids such as body fluids.

Accordingly, in one embodiment the present invention can be useful for coating medical devices, where a slippery exterior and/or interior, are necessary or desirable to minimize injury to tissues and to aid in manipulation of the devices during surgical procedures.

Exemplary medical devices include catheters, needles, guide wires, prophylactic devices, delivery systems, filters, sheaths, and other accessories employed in medical diagnostics, drainage, dilatation occlusion, vena cava, oncology, ophthalmology, orthopedics, reconstructive surgery, anesthesiology, dermatology, dental, ENT, vascularport infusion devices, phlebotomy, critical care vascular access, and the like.

In the examples which follow, the polyisocyanate employed was an aromatic isocyanate end-capped prepolymer, average NCO equivalent weight 182. The poly(carboxylic acid) was a USP grade poly(acrylic acid) partially cross-linked homopolymer having a molecular weight of about 1,250,000 to about 3,000,000. These compounds and the other compounds employed in the Examples are readily available from commercial sources.

A polyisocyanate primer solution (A) was prepared by mixing 83.2 parts of MEK (Mallinckrodt), 15 parts of mineral oil (Malincrodt), 1.8 parts of the polyisocyanate to yield a mobil, clear liquid. The solution contained 0.42% by weight of isocyanate groups.

Another polyiscyanate primer solution (B) was prepared by mixing 98.2 parts of MEK (Mallinckrodt) and 1.8 parts of the polyisocyanate to yield a mobil clear liquid. The solution contained 0.42% by weight of isocyanate groups.

A low viscosity, uniform colloidal dispersion of the poly(acrylic acid) was prepared by the following procedure: Into a 2-liter stainless steel reactor, equipped with a turbine agitator, condenser, thermometer, and an exterior heating bath, there was charged under agitation 487.17 grams of DMF (Mallinckrodt), 252.7 grams of MEK (Mallinckrodt), 234.3 grams of tertiary butyl alcohol, and 0.83 grams of MYRJ-53 (an ethoxylated steric acid produced by ICI). Once a uniform solution was obtained, 25 grams of the poly(acrylic acid) powder were introduced by pouring directly into the reactor, The reactor was heated to 50° C. and maintained at 50°±2° C. for one hour while under agitation at 2000 rpm. Thereafter, the reactor was cooled to room temperature and the content was transferred into a Waring Blender for homongenization. The homogenized product was filtered through a 10 micron polypropylene filter cartridege to yield a uniform colloidal dispersion. It showed the following viscosity properties:

| Before homogenization | |
|---|---|
| Brookfield viscosity | 40 centipoises |
| Kinematic viscosity | 17.3 centistokes |
| After homogenization | |
| Brookfield viscosity | 7 centipoises |
| Kinematic viscosity | 8.7 centistokes |

The following examples are illustrative of the invention.

EXAMPLE 1

This example illustrates the polymeric complex formation between two water soluble polymers, one being poly(ethylene oxide) (PEO) and the other being poly(acrylic acid) (PAA).

An aqueous solution of PAA was prepared by dissolving 5 gms of the poly(acrylic acid) and 0.0025 gm of a polyoxyethylene stearate surfactant in one liter of distilled water. The finished solution showed a Brookfield viscosity (Model LTV, 30 rpm at 20.7° C.) of 720 centipoises. An aqueous solution of PEO was prepared by dissolving 20 gm of POLYOX WSR 750 NF (trademark for a poly(ethylene oxide) produced by Union Carbide) and 0.01 gm of the surfactant in one liter of distilled water. The finished solution showed a Brookfield viscosity of 70 centipoises.

A series of mixtures were prepared from the above-mentioned polymeric solutions such that the weight ratio of PEO/PAA varies from 9/1 to 1/9. The characteristics of the resultant polymeric complexes are summarized in Table 1 below:

| PEO/PAA Weight Ratio | Brookfield Solution Viscosity, cps | Characteristics |
|---|---|---|
| 10/0 | 70 | clear solution |
| 9/1 | 1,100 | clear solution |
| 8/2 | 520 | hazy solution |
| 7/3 | — | insoluble complex |
| 6/4 | — | insoluble complex |
| 5/5 | — | insoluble complex |
| 4/6 | — | insoluble complex |
| 3/7 | — | insoluble complex |
| 2/8 | 20 | hazy dispersion |
| 1/9 | 270 | hazy dispersion |
| 0/10 | 720 | clear solution |

EXAMPLE 2

This example illustrates the polymeric complex formation between poly(vinyl pyrrolidone) (PVP) and poly(acrylic acid) (PAA).

An aqueous solution of PAA was prepared by dissolving 10 gms of the poly(acrylic acid) and 0.005 gm of a polyoxyethylene stearate surfactant in one liter of distilled water. The finished solution showed a Brookfield viscosity (Model LTV, 30 rpm at 21° C.) of 1860 centipoises. An aqueous solution of PVP was prepared by dissolving 10 gm of PVP-360 (Sigma Chemical Company) and 0.0026 gm of a polyoxyethylene stearate surfactant in one liter of distilled water. The finished solution showed a Brookfield viscosity of 102 centipoises.

A series of mixtures were prepared from the above-mentioned polymeric solutions such that the weight ratio of PVP/PAA varies from 9/1 to 1/9. The characteristics of the resultant polymeric complexes are summarized in Table 2 below:

| PVP/PAA Weight Ratio | Brookfield Solution Viscosity, cps | Characteristics |
| --- | --- | --- |
| 10/0 | 4 | clear solution |
| 9/1 | exceeded 100,000 cps | dense gel |
| 7/3 | exceeded 100,000 cps | dense gel |
| 5/5 | 5350 | soft gel |
| 3/7 | 5900 | soft gel |
| 1/9 | 4850 | soft gel |
| 0/10 | 1860 | clear solution |

EXAMPLE 3

This example consisting of Parts A and B illustrates the preparation of a lubricious coating using a PEO-PAA complex.

Part A

Six pieces of a flexible, plastic catheter (7 French C-Flex catheter produced by Concept Polymer) were coated with a PAA base coating according to the following procedure:

1. Wipe the surface with a cleaning solvent.
2. Dip in an aromatic isocyanate end-capped prepolymer having an average NCO equivalent weight 182 (polyisocyanate primer solution A).
3. Bake in a forced air oven at 60° C. for 30 minutes.
4. Dip in the dispersion of a poly(acrylic acid) partially cross-linked homopolymer having a molecular weight between about 1,000,000 to 3,000,000
5. Bake in a forced air oven at 60° C. for 60 minutes.

The finished coating was uniform, clear and adherent to the surface of the catheter.

Part B

A 1% by weight of poly(ethylene oxide) (POLYOX WSR 750 NF produced by Union Carbide) solution in toluene was prepared by mixing while warming gently on a hot plate. A clear solution was obtained.

Four pieces of the coated catheter were treated with the 1% PEO solution by dipping in the solution for 10 seconds and followed by drying in a forced air oven at 60° C. for 30 minutes. The dried catheters exhibited a normal feel to the touch. They became very lubricious, however, upon exposure to water. They exhibited a wet frictional coefficient of 0.05 against 0.5 for the original C-Flex catheters.

EXAMPLE 4

This example illustrates the preparation of a lubricious coating using a PVP-PAA complex.

A 1% by weight of PVP (Plasdone C-15, produced by GAF) solution in methylene chloride was prepared by mixing while warming gently on a hot plate. A clear solution was obtained.

Six pieces of the same plastic catheter described in Example 3 were coated with the same polyisocyanate primer solution (A) and poly(acrylic acid) according to the procedure mentioned in Example 3, Part A.

Four pieces of the coated catheters were treated with the 1% PVP solution by dipping in the solution for 10 seconds and followed by drying in a forced air oven at 60° C. for 30 minutes. The dried catheters exhibited a normal feel to the touch. They became very lubricious, however, upon exposure to water. They exhibited a wet frictional coefficient of 0.03 against 0.5 for the original C-Flex catheter.

EXAMPLE 5

This and the following examples illustrate the preparation of a PEO-iodine coating. Six grams of poly(ethylene oxide) (POLYOX WSR 750 NF produced by Union Carbide) was dissolved in 594 gm of toluene with mixing and gentle heating. Thereafter, 4.5 gm of iodine was added to yield a brownish solution. The molar ratio of PEO to iodine was 1:0.17.

EXAMPLE 6

Example 5 was repeated with the exception that the weights of PEO, toluene, and iodine used were 24, 709.8 and 66.2 respectively. The molar ratio of PEO to iodine was 1:0.5 in the finished solution.

EXAMPLE 7

This and the following example illustrate the preparation of a PVP-iodine coating solution.

Six grams of poly(vinylpyrrolidone) (Plasdone C-15 produced by GAF) was dissolved in 594 gm of methylene chloride with mixing and gentle heating. Thereafter, 3.45 gm of iodine was added to yield a brownish solution. The molar ratio of PVP to iodine was 1:0.25.

EXAMPLE 8

Example 7 was repeated with the exception that the weights of PVP, methylene chloride, and iodine used were 24, 721.61, and 54.39 gm, respectively. The molar ratio of PVP to iodine was 1:1 in the finished solution.

EXAMPLE 9

This and the following three examples illustrate the preparation of a lubricious coating having antimicrobial agent in the form of either PEO-iodine or PVP-iodine complex.

Twelve pieces of 9.5 inch long C-Flex catheters were coated with the same polyisocyanate primer solution A and poly(acrylic acid) according to the procedure described in Example 3. The coated catheters were subsequently treated with the PEO-iodine solution of Example 5 following the method described in Example 3. The finished catheters exhibited a normal feel to the touch and a bluish color in an aqueous starch solution indicating the presence of iodine. The coating developed lubricity upon exposure to water, and showed a wet frictional coefficient of 0.03 in distilled water against a much higher frictional coefficient of 0.5 for the original uncoated catheters.

EXAMPLE 10

Twelve pieces of 9.5 inch long C-Flex catheters were coated with the same polyisocyanate primer solution A and poly(acrylic acid) according the procedure described in Example 3. The coated catheters were subsequently treated with the PEO-iodine solution of Example 7 following the method described in Example 4. The finished catheters exhibited a normal feel to the touch and a bluish color in an aqueous starch solution indicating the presence of iodine. The coating developed lubricity upon exposure to water and showed a wet frictional coefficient of 0.03 in distilled water against a much higher frictional coefficient of 0.5 for the original uncoated catheters.

EXAMPLE 11

Five pieces of 9.5 inch long C-Flex catheters were coated with the same polyisocyanate primer solution A and poly(acrylic acid) according the procedure described in Example 3 with the exception that a 85° C. baking temperature was used. The coated catheters were treated with the PEO-iodine solution of Example 6 following the method described in Example 3. The finished catheters exhibited a normal feel to the touch and a bluish color in an aqueous starch solution indicating the presence of iodine. The coating developed lubricity upon exposure to water, and showed a much lower frictional coefficient than that of the original uncoated catheter.

EXAMPLE 12

Five pieces of 9.5 inch long C-Flex catheters were coated with the same polyisocyanate primer solution A and poly(acrylic acid) according the procedure described in Example 11. The coated catheters were treated with the PVP-iodine solution of Example 8 following the method described in Example 4. The finished catheters exhibited a normal feel to the touch and a bluish color in an aqueous starch solution indicating the presence of iodine. The coating developed lubricity upon exposure to water, and showed a much lower frictional coefficient than that of the original uncoated catheter.

EXAMPLE 13

The PAA PEO-iodine coated catheters prepared in Example 11 were analyzed for organism growth inhibition by dipping each catheter for 10 seconds into solutions of *Pseudomonas aeruginosa* and *Staphylococcus aureus* containing approximately $10^6$ organisms /ml. After 10 seconds, excess drops of solution were drained off and the catheters were placed into TGE broth (tryptone glucose extract supplied by Ditco Laboratories) and were vortexed for 10 seconds. One ml of each broth was plated out and incubated for 48 hours at 37° C. Uncoated catheters were treated in an identical manner. Growth inhibition is defined as log(number of organisms on uncoated catheters)−log(number of organisms on coated catheters). The results are shown as follows:

| Organism Type | Growth Inhibition |
| --- | --- |
| *Staphylococcus aureus* | 2.4 log reduction |
| *Pseudomonas aeuginosa* | 3.2 log reduction |

EXAMPLE 14

The PVP-iodine coated catheters prepared in Example 12 were analyzed for organism growth inhibition by the same method as described in Example 13. The results are shown as follows:

| Organism Type | Growth Inhibition |
| --- | --- |
| *Staphylococcus aureus* | 2.7 log reduction |
| *Pseudomonas aeuginosa* | complete kill |

EXAMPLE 15

The PAA-PEO-iodine coated catheters prepared in Example 9 were tested for lubricity in different pH solutions and the results are shown as follows:

| pH | Wet Frictional Coefficient |
| --- | --- |
| 7 (distilled water) | 0.03 |
| 5 (buffer solution) | 0.03 |
| 4 (buffer solution) | 0.09 |

Uncoated catheters showed a much higher wet frictional coefficient of 0.5 at all three pH values.

EXAMPLE 16

The PAA-PVP-iodine coated catheters prepared in Example 10 were tested for lubricity in different pH solutions and the results are shown as follows:

| pH | Wet Frictional Coefficient |
| --- | --- |
| 7 (distilled water) | 0.05 |
| 5 (buffer solution) | 0.03 |
| 4 (buffer solution) | 0.07 |

Uncoated catheters showed a much higher wet frictional coefficient of 0.5 at all three pH values.

EXAMPLE 17

This example illustrates the preparation of a mixture containing both PEO and PVP in a common solvent.

Mixing 6 gm of PEO (POLYOX 750 NF, produced by Union Carbide) and 594 gm of methylene chloride (Mallinckrodt) with gentle heating until a clear solution was obtained. Another solution containing 6 gm of PVP (Plasdone C-15, produced by GAF) and 594 gm of methylene chloride was prepared in the same manner. The two solutions were subsequently combined to yield a solution containing 0.5% by weight of each of PEO and PVP.

EXAMPLE 18

This example illustrates the utility of a mixture of polymeric complexes to afford either a hydrophilic lubricious coating or such a coating with antimicrobial activity.

Bismuth carbonate filled Nylon catheters were coated with polyisocyanate primer solution B and poly(acrylic acid) following the procedure described in example 11. The coated catheters were treated with the PEO/PVP mixture solution of Example 17 following the procedure described in Example 4 with the exception that the baking was carried out at 85° C. The treated catheters were divided into two groups. Group A catheters were tested without further treatment. Group B catheters were dipped for a 10 second period into a 1% iodine solution in methylene chloride and followed by a 30 minute drying in a forced air oven at 60° C.

The Group A catheters showed a mean wet frictional coefficient of 0.07, and the Group B catheters showed a mean wet frictional coefficient of 0.06. The original uncoated C-flex catheters possessed a wet frictional coefficient of 0.5.

EXAMPLE 19

This example illustrates the preparation of a coating solution containing a poly(methyacrylic acid).

Into a one-liter size Pyrex-glass reactor equipped with a turbine agitator, a thermometer, a condenser, an external heating bath and an addition funnel there was charged 312 gm of dimethylformamide, 158.7 gm of methyl ethyl ketone, 120 gm of t-butyl alcohol, 0.3 gm of MYRJ-53 surfactant (polyethoxylated stearate produced by ICI), and 9 gm of poly(methacrylic acid) (supplied by Polysciences). The mixture was heated to 50° C. while under vigorous mixing. After 1 hour mixing at 50° C., a uniform dispersion was obtained, the reactor was cooled down to room temperature, and the product was filtered through a ten micron size filter. The finished liquid dispersion prossessed a kinematic solution viscosity of 1.7 centistokes at 25° C. measured with a Cannon-Fencke viscosimeter.

EXAMPLE 20

This example illustrates the utility of PMA-PEO complex for forming a hydrophilic lubricious coating.

Six pieces of 7 French C-flex catheters were coated with the same polyisocyanate of Example 3 and the PMA coating solution described in Example 19 according to the procedure mentioned in Example 3. The coated catheters were treated with a 1% PEO (POLYOX WSR 750 NF produced by Union Carbide) solution in methylene chloride following the procedure described in Example 3, Part A. The surface of the finished coating felt normal to the touch, but became lubricious when exposed to water. It showed a wet frictional coefficient of 0.08 against 0.5 for the original uncoated catheter.

The following Examples 21-24 illustrate the coating process of the present invention wherein the coating process uses an aqueous solution of either PEO or PVP.

EXAMPLE 21

An aqueous PEO solution was prepared by dissolving 7 grams of PEO (POLYOX WSR 750 NF produced by Union Carbide) in 693 grams of distilled water. The resultant solution showed a Brookfield viscosity (Model LVT, 30 rpm at 28° C.) of 5 cps.

EXAMPLE 22

An aqueous PVP solution was prepared by dissolving 7 grams of PVP (PVP K-90 produced by GAF) in 693 grams of distilled water. The resultant solution showed a Brookfield viscosity (Model LVT, 30 rpm at 28° C.) of 3.2 cps.

EXAMPLE 23

Two pieces of 7 French C-Flex catheters were coated with the same polyisocyanate and poly(acrylic acid) according to the procedure described in Example 3, Part A. One piece of the coated catheter was treated with the aqueous PEO solution of Example 21 for 10 seconds and followed by a 60° C. bake for 30 minutes. The PEO coated catheter was dipped once more in an 1% iodine solution in methylene chloride and followed by a 30 minute bake at 60° C. The catheter showed a weight gain of PEO and iodine pickup of 0.2% and 0.48% respectively. The finished catheter exhibited a normal feel to the touch, but became somewhat lubricious once exposed to water or body fluids. However, the lubricity was significantly reduced compared to a catheter coated only with poly(acrylic acid). When it was immersed into a starch solution, it produced a characteristic bluish color of an iodine complex.

EXAMPLE 24

The second piece of coated C-Flex catheter of Example 23 was treated with the aqueous PEO solution of Example 21 for one minute and followed by a 60° C. bake for 30 minutes. The PEO coated catheter was dipped once more in an 1% iodine solution in methylene chloride and followed by a 30 minute drying at 60° C. by weight gain, the catheter showed a PEO and iodine pickup of 0.75 and 0.47% respectively. While useful as an antimicrobial, these catheters were not lubricious.

EXAMPLE 25

Example 23 was repeated with the exception that the coated catheter was treated with the aqueous PVP solution of Example 22. by weight gain, the catheter showed a PVP and iodine pickup of 0.86 and 2.5% respectively. The finished catheter showed a characteristic bluish color of iodine in a starch solution.

EXAMPLE 26

Example 24 was repeated with the exception that the coated catheter was treated with the aqueous PVP solution of Example 22. By weight gain, the catheter showed a PVP and iodine pickup of 0.71 and 2.4% respectively. The finished catheter showed a characteristic bluish color of iodine in a starch solution.

EXAMPLE 27

This example illustrates the preparation of a poly(acrylic acid) and poly(alkylene oxide) samples where the latter is an (ethylene oxide-propylene oxide) copolymer identified commercially as UCON lubricant 75-H-90,000, produced by Union Carbide Corporation.

Six pieces of the same plastic catheter described in Example 3, Part A, were coated according to the procedure described in that example.

An aqueous solution containing 2% by weight of the (ethylene oxide-propylene oxide) copolymer was prepared by mixing on a roll mill until a homogeneous solution was obtained. The solution exhibited a Brookfield viscosity of 1 cps at 25° C.

The above coated catheters were dipped into a bath containing the (ethylene oxide-propylene oxide) copolymer for a 10 second period. The wet catheters were air dried for 1 minute and placed in a forced air oven at 65° C. for 30 minutes. The finished coating was smooth, and became moderately lubricious upon exposure to water.

EXAMPLE 28

This example describes the instruments used for measuring the Frictional Coefficient of the coating in the presence of water. (see also European patent application 0166998, filed Jun. 4, 1985).

A pair of coated catheters is laid parallel to each other on a horizontal stainless steel platform at a distance of about 1.5 inches apart. The platform and the catheters are subsequently wetted with about 100 ml of distilled water. A rectangular shaped aluminum block (2×2×3") weighing 100 grams wrapped in a wet cellulose acetate membrane is placed on top of the catheters at the free moving end of the platform. Thereafter, the platform is raised from the free-moving end until an inclination angle θ is reached where the block begins to slide on the wet catheters surfaces. Frictional coefficient is calculated as follows:

frictional coefficent = tangent θ

The test is normally conducted between a sliding angle of 1° to 12° which corresponds to a frictional coefficient value between 0.02 to 0.2. Any higher frictional surface is recorded as having a frictional coefficient of >0.2.

EXAMPLE 29

This example illustrates the abrasion test conducted to evaluate the adhesion of the wet coating to the substrate.

A coated catheter is rubbed with a piece of wet tissue (Kimwipes, Kimberly Clark) folded to about 2×2" in size and wrapped around the circumference of the catheter. Finger pressure is applied to the wet wrapping against the catheter surface, and the wrapping is pulled longitudinally from one end to the other. After ten rubs have been made, a pair of the abraded catheters are retested for Frictional Coefficient according to the procedure described in Example 28. Adhesion of the wet coating is judged by the extent of change in frictional coefficient after the abrasion test.

EXAMPLE 30

The following experiments demonstrate the effectiveness of anchoring poly(ethylene oxide) on the surface of a medical device by the method described herein.

Different groups of C-Flex catheters, either coated according to the procedure described in Example 3, Part A, or coated only with primer solution (B), or uncoated were treated with a 1% poly(ethylene oxide) (Union Carbide POLYOX N-750) in either methylene chloride or water. The characteristics of the finished coatings are listed in Table 1.

TABLE I

| Example | Coating Applied | PEO Solution | Frictional Coefficient before-after | | Surface Characteristics |
|---|---|---|---|---|---|
| 30-1 | none | water | >0.2 | >0.2 | hydrophobic |
| 30-2 | none | methylene chloride | >0.2 | >0.2 | hydrophobic |
| 30-3 | polyisocyanate primer(B) | methylene chloride | 0.12 | >0.2 | hydrophilic |
| 30-4 | according to Example 3 (Part B) | water | 0.06 | 0.06 | hydrophilic. |

The C-flex catheters treated according to Examples 30-1 and 30-2 were neither lubricious nor hydrophilic; an indication of practically no absorbed poly(ethylene oxide) on the surface of these catheters. The surface of the C-Flex catheters treated in Example 30-3 were hydrophilic and moderately lubricious. The catheters lost nearly all their lubricity after the abrasion test indicating a lack of adhesion to the substrate. The surface of the catheters treated in Example 30-4 were both hydrophilic and lubricious, the latter remained unchanged after the abrasion test.

EXAMPLE 31

The following examples illustrate the effectiveness of bonding a (ethylene oxide-propylene oxide) copolymer (Union Carbide UCON 75H90,000) on the surface of a medical device by the method described herein by procedures similar to those described in example 30. A 2% (ethylene oxide-propylene oxide) copolymer solution in either methylene chloride or water was employed.

TABLE II

| Example | Coating Applied | PEO Solution | Frictional Coefficient before-after | | Surface Characteristics |
|---|---|---|---|---|---|
| 31-1 | none | water | >0.2 | >0.2 | hydrophobic |
| 31-2 | none | methylene chloride | >0.2 | >0.2 | hydrophobic |
| 31-3 | polyisocyanate primer(B) | methylene chloride | 0.12 | >0.2 | hydrophobic |
| 31-4 | according to Example 27 | water | 0.06 | 0.06 | hydrophilic |

In the above examples, only the surface of the catheters treated in Examples 31-4 was hydrophilic and lubricious. The frictional coefficient before and after abrasion was identical.

EXAMPLE 32

The following examples demonstrate the effectiveness of anchoring a poly(vinyl pyrrolidone) (SIGNA PVP-360) on the surface of a medical device by the method described herein using procedures similar to those described in Example 30. A 2% poly(vinyl pyrrolidone) solution in either methylene chloride or water was employed.

TABLE III

| Example | Coating Applied | PVP Solution | Frictional Coefficient before-after | | Surface Characteristics |
|---|---|---|---|---|---|
| 32-1 | none | water | >0.2 | >0.2 | hydrophobic |
| 32-2 | none | methylene chloride | >0.2 | >0.2 | hydrophobic |
| 32-3 | polyisocyanate primer (B) | methylene chloride | >0.2 | >0.2 | hydrophilic |
| 32-4 | according to Example 3 Part B | water | 0.1 | 0.12 | hydrophilic |

Examples 32-1 and 32-2 showed little PVP absorption on the surface of the catheters. The surface of catheters treated in Example 32-3 showed only hydrophilicity but little lubricity. Again, the surface of the catheter treated in Example 32-4 was both hydrophilic and lubricious.

EXAMPLE 33

The surface of the coated catheters prepared in Examples 30-4, 31-4, and 32-4 were examined with a FTIR spectroscope. The presence of the desired polymer complexes was supported by the following evidence.

TABLE IV

| Example | Complex Type | Carbonyl Frequency, cm$^{-1}$ | Ether or Nitrile Frequency, cm$^{-1}$ |
|---|---|---|---|
| 30-4 | Poly(acrylic acid) Poly(ethylene oxide) | to 1710 | 1247 1160 1103 |
| | Poly(acrylic acid) only | 1706 | 1251 1169 |
| | Poly(ethylene oxide) only | — | 1096 |
| 31-4 | Poly(acrylic acid)-(ethylene oxide-propylene oxide) copolymer | 1727 | 1247 1098 1093 |
| | (ethylene oxide-propylene oxide) copolymer only | — | 1111 |
| 32-4 | Poly(acrylic acid)-Poly(vinyl pyrrolidone) | 1658 | 1289 |
| | Poly(vinyl pyrrolidone) only | 1680 | 1271 1284 |

Although the invention has been illustrated by the preceding examples, it is not to be construed as being limited to the materials desclosed therein, but rather, the invention is directed to the generic area as hereinbefore disclosed. Various modifications and embodiments thereof can be made without departing from the spirit or scope thereof.

We claim:

1. A method of covering at least a portion of a substrate with a hydrophilic polymeric complex to provide a biocompatible surface said method consisting essentially of:
   (1) contacting said substrate with a polyisocyanate contained in a first inert solvent to provide at least a partially coated substrate;
   (2) contacting said coated substrate with a carboxylic acid containing polymer contained in a second inert solvent to provide a multiple coated substrate and optionally one or more additives selected from the group consisting of stabilizers, antioxidants, antimicrobial agents, antithrombogenic agents, colorants and biological agents;
   (3) contacting said multiple coated substrate with a third inert solvent containing at least one member of the group consisting of a poly (N-vinyl lactam) and a poly (lower-alkylene oxide) and optionally one or more additives selected from the group consisting of stabilizers, antioxidants, antimicrobial agents, antithrombogenic agents, colorants and biological agents; and
   (4) thereafter drying said multiple coated substrate.

2. The method of claim 1 wherein said substrate coated with said polyisocyanate is dried at a temperature of up to about 150° C. before step (2).

3. The method of claim 1 wherein said multiple coated substrate provided by step (2) is first dried at a temperature of from about 15° to about 150° C. after completion of step (2) and before step (3).

4. The method of claim 1 wherein said first solvent is a ketone.

5. The method of claim 1 wherein said first solvent is a hydrocarbon.

6. The method of claim 1 wherein said first solvent is a mixture of at least two solvents.

7. The method of claim 1 wherein said second inert solvent additionally contains at least one surfactant.

8. The method of claim 1 wherein said second solvent is dimethylformamide.

9. The method of claim 1 wherein said second solvent is a mixture of dimethylformamide and methyl ethyl ketone.

10. The method of claim 1 wherein said second solvent is a mixture of dimethylformamide, methyl ethyl ketone, and t-butyl alcohol.

11. The method of claim 1 wherein said third solvent is water or an organic solvent.

12. The method of claim 1 wherein said polyisocyanate is a diisocyanate.

13. The method of claim 12 wherein said diisocyanate is a mixture of toluene 2,4- and 2,6-diisocyanate.

14. The method of claim 12 wherein said diisocyanate is a diphenylmethane diisocyanate.

15. The method of claim 12 wherein said diisocyanate is an adduct of diphenylmethane diisocyanate and a polyol.

16. The method of claim 1 wherein said polyisocyanate is an isocyanate end-capped polyfunctional aliphatic adduct.

17. The method of claim 1 wherein said polyisocyanate is an isocyanate end-capped polyfunctional aromatic adduct.

18. The method of claim 1 wherein said polyisocyanate is a reaction product of a polyfunctional isocyanate with a polyester polyol.

19. The method of claim 1 wherein said polyisocyanate is a reaction product of a polyfunctional isocyanate with an aromatic polyether polyol.

20. The method of claim 1 wherein said polyisocyanate is a mixture of a diisocyanate and an isocyanate end-capped polyfunctional adduct.

21. The method of claim 1 wherein said carboxylic acid-containing polymer is a colloidal dispersion of a homopolymer.

22. The method of claim 1 wherein said carboxylic acid-containing polymer has a molecular weight of from about 200,000 to about 5,000,000.

23. The method of claim 1 wherein said carboxylic acid-containing polymer is a poly(acrylic acid).

24. The method of claim 1 wherein said carboxylic acid-containing polymer is a poly(methacrylic acid).

25. The method of claim 1 wherein said carboxylic acid-containing polymer is a copolymer.

26. The method of claim 1 wherein said carboxylic acid containing polymer is partially cross-linked and contains at least some water insoluble units.

27. The method of claim 1 wherein said polyisocyanate is applied as a dispersion.

28. The method of claim 1 wherein said carboxylic acid containing polymer is applied as an emulsion.

29. The method of claim 1 wherein said carboxylic acid containing polymer is applied as a solution.

30. The method of claim 1 wherein said poly(lower-alkylene oxide) component is a polymer comprised of at least about 50 weight percent of poly(ethylene oxide).

31. The method of claim 30 wherein said polymer is a homopolymer of ethylene oxide.

32. The method of claim 30 wherein said polymer is a copolymer of ethylene oxide and a second lower alkylene oxide.

33. The method of claim 1 wherein said poly(N-vinyl lactam) component is pol(vinyl pyrrolidone).

34. A method of covering at least a portion of a substrate with a hydrophilic polymeric complex to provide a biocompatible surface said method consisting essentially of:
(1) contacting said substrate with a polyisocyanate contained in a first inert organic solvent to provide at least a partially coated substrate;
(2) contacting said coated substrate with a poly(acrylic acid) polymer of the formula:

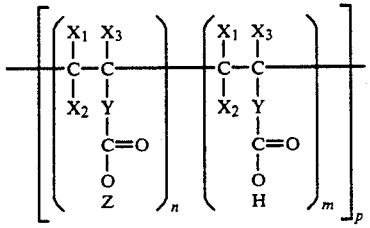

where
$n = 0–0.95$ mole fraction of neutralized acid moieties;
$m = 0.05–1.0$ mole fraction of acid moieties with the proviso that $n = m = 1$;
$X_1, X_2, X_3$ are each a hydrogen atom or a monovalent organic radical;
Y is a single bond or a divalent organic radical;
Z is a metallic ion or a tertiary ammonium ion; and
p is a number such that the polymer has a molecular weight between about 200,000 and about 5,000,000;
said poly(acrylic acid) contained in a second inert organic solvent to provide a multiple coated substrate;
(3) contacting said multiple coated substrate with a third solvent containing at least one polymeric compound selected from the group consisting of a poly(vinyl pyrrolidone) and a poly(ethylene oxide); and
(4) thereafter drying said multiple coated substrate.

35. The method of claim 34 where said third solvent is a mixture of dimethylformamide, methyl ethyl ketone and tertiary butyl alcohol.

36. A method of covering at least a portion of a substrate with a hydrophilic polymeric complex to provide a biocompatible surface said method consisting essentially of:
(1) contacting said substrate with a blend of a polyisocyanate and a poly(acrylic acid) polymer of the formula:

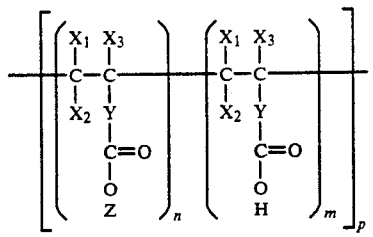

where
$n = 0–0.95$ mole fraction of neutralized acid moieties;
$m = 0.05–1.0$ mole fraction of acid moieties with the proviso that $n + m = 1$;
$X_1, X_2, X_3$ are each a hydrogen atom or a monovalent organic radical;
Y is a single bond or a divalent organic radical;
Z is a metallic ion or a tertiary ammonium ion; and
p is a number such that the polymer has a molecular weight between about 200,000 and about 5,000,000;
said blend of polyisocyanate and poly(acrylic acid) contained in an inert organic solvent in which said polyisocyanate and poly(acrylic acid) are dispersible;
(2) contacting said multiple coated substrate with a second solvent containing at least one polymeric compound selected from the group consisting of a poly(vinyl pyrrolidone) and a poly(ethylene oxide); and
(3) thereafter drying said multiple coated substrate.

37. The method of claim 1 wherein said additive is an antithrombogenic agent.

38. The method of claim 1 wherein said additive is heparin.

39. The method of claim 1 wherein said additive is an antimicrobial agent.

40. The method of claim 1 wherein said antimicrobial agent is iodine.

41. A coated substrate having at least a portion thereof coated by the method of claim 1.

42. The coated substrate of claim 41 which is a medical device.

43. The substrate of claim 41 which is a medical device suitable for implantation in the human body.

44. The medical device of claim 42 which is a catheter.

45. The medical device of claim 42 which is a guide wire.

* * * * *